Figure 1:
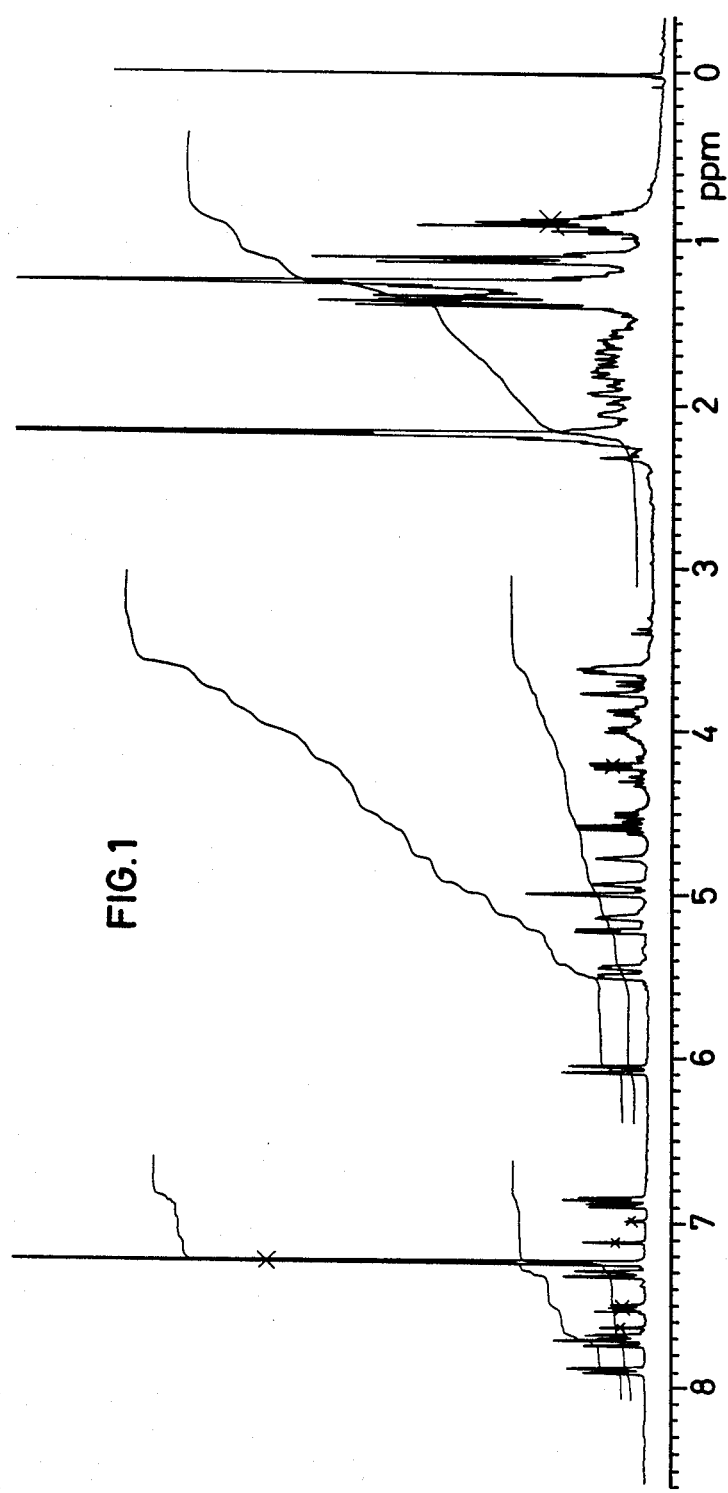

United States Patent [19]

Berscheid et al.

[11] Patent Number: 4,795,808
[45] Date of Patent: Jan. 3, 1989

[54] ANTHRACYCLINE TETRASACCHARIDES

[75] Inventors: Hans G. Berscheid, Schwalbach am Taunus; Dirk Böttger, Liederbach; Hans P. Kraemer, Marburg, all of Fed. Rep. of Germany

[73] Assignee: Hoechst Aktiengesellschaft, Frankfurt, Fed. Rep. of Germany

[21] Appl. No.: 933,885

[22] Filed: Nov. 24, 1986

Related U.S. Application Data

[63] Continuation-in-part of Ser. No. 881,662, Jul. 3, 1986, abandoned.

[51] Int. Cl.[4] .............................................. C07H 15/24
[52] U.S. Cl. ...................................................... 536/6.4
[58] Field of Search ........................... 536/6.4; 514/34

[56] References Cited

U.S. PATENT DOCUMENTS 4,207,313  6/1980  Umezawa et al. ............... 514/34
4,373,094  2/1983  Oki et al. ........................ 514/34
4,713,371  12/1987 Aretz et al. ..................... 514/34
4,737,583  4/1988  Huber et al. ................... 536/6.4

FOREIGN PATENT DOCUMENTS 0063776  11/1982  European Pat. Off. ........ 536/6.4
0078446  5/1983   European Pat. Off. ........ 536/6.4
0078447  5/1983   European Pat. Off. ........ 536/6.4

Primary Examiner—J. R. Brown
Assistant Examiner—Elli Peselev
Attorney, Agent, or Firm—Finnegan, Henderson, Farabow, Garrett & Dunner

[57] ABSTRACT

The present invention relates to anthracycline derivatives and a process for their preparation. The compounds are distinguished by a high cytostatic activity and can therefore be used as medicaments with an antitumor action.

7 Claims, 3 Drawing Sheets

ANTHRACYCLINE TETRASACCHARIDES

This is a continuation-in-part-application of copending application Ser. No. 881,662 filed July 3, 1986 by Berscheid et al, now abandoned.

The present invention relates to anthracycline derivatives of the formula I

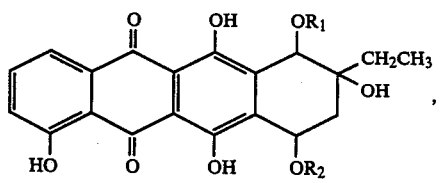

in which $R_1$ and $R_2$ are different and one of the two radicals represents the sugar unit L-rhodosamine (Roa) of the formula

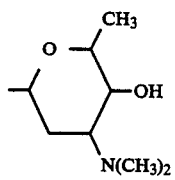

while the other represents the sugar combination L-rhodosamine-L-rhodinose-L-rhodinose (Roa—Rod—Rod) of the formula

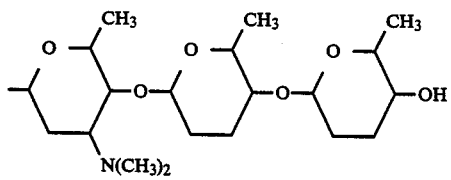

or L-rhodosamine-L-rhodinose-L-aculose (Roa—Rod—Acu) of the formula

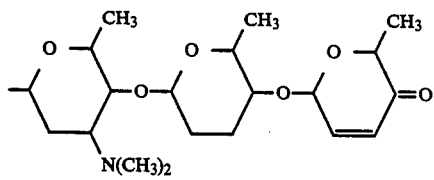

or L-rhodosamine-2-deoxy-L-fucose-L-cinerulose A (Roa—dF—Cin—A) of the formula

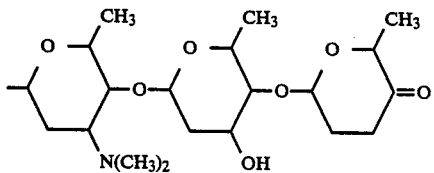

The present invention furthermore relates to a process for the preparation of the compounds of the formula I, which comprises splitting off the terminal disaccharide in one of the two trisaccharide chains in one of the compounds, described in European Patent No. A-0,131,181 (HOE 83/F 103), of the formula II

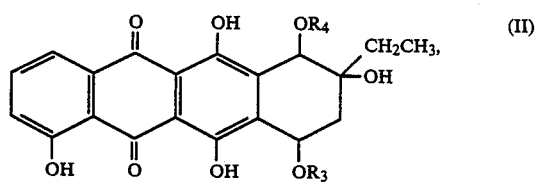

in which one of the two substituents $R_3$ and $R_4$ denotes one of the sugar combinations Roa—Rod—Rod, Roa—Rod—Acu or Roa—dF—CinA and the other substituent denotes one of the sugar combinations Roa—Rod—Rod, Roa—Rod—Acu, Roa—dF—CinA, Roa—dF—Rod or Roa—dF═CinB, CinB representing cinerulose B and dF═CinB denoting that the two sugar units are linked by an extra ether bridge in addition to the customary glycosidic bond, by treatment with an acid.

According to European Patent No. A-0,131,181, the strain Steptomyces purpurascens DSM 2658 is fermented in a nutrient medium in the customary manner, temperatures of about 24°-40° C., a pH of 6.5-8.5 and aerobic conditions being maintained. The anthracycline compounds are extracted from the mycelium, for example with aqueous acetone at pH 3.5, the acetone is removed and the aqueous phase is extracted with ethyl acetate at a pH of 7.5. the culture liquid is extracted at pH 7.5, preferably with ethyl acetate. The ethyl acetate extracts from the mycelium and the culture filtrate are combined and give, when evaporated to dryness, a crude residue. The residue thus obtained can now be subjected to acid treatment as described in European Patent Application No. EP-A 0,131,942 (HOE 83/F 139). Preferably, however, the residue is worked up further, as described in European Patent No. A-0,131,181.

The crude residue is accordingly dissolved in toluene and extracted with an acetate buffer (pH 3.5), a toluene phase and an aqueous phase being obtained. The aqueous phase is further worked up as follows: after bringing the pH to 7.5, extraction is again carried out with ethyl acetate and the ethyl acetate phase is concentrated, a so-called crude cytorhodin mixture being obtained. According to the European Patent Application mentioned, anthracycline hexasaccharides of the formula II can be obtained from this crude mixture by chromatography.

European Patent No. A-0,131,142 (HOE 83/F 139) describes that novel anthracycline tetrasaccharides which are just as active are obtained if the crude residue of anthracycline hexasaccharides described above, the so-called crude cytorhodin mixture, is treated with acid. Surprisingly, it is now possible to obtain further novel, previously unknown hydrolysis products with an anthracycline tetrasaccharide structure on acid treatment of isolated pure components which have been described in European Patent No. A-0,131,181.

Examples of suitable acids are dilute hydrochloric acid, sulfuric acid, phosphoric acid, formic acid, acetic acid and other acids, if appropriate also after addition of a water-miscible organic solvent, for example methanol or acetone. The acid treatment can also be carried out with strongly acid ion exchangers in the H form, such as, for example, Dowex 50×8 (H+). In this case, the desired product must be obtained by elution from the ion exchanger, for example with salt solutions.

The treatment with acid is carried out at room temperature or slightly elevated temperature, preferably 37° C. The reaction time can be 0.5 to several hours, but is different for each of the compounds, as has been found by experiments on the reaction kinetics. When the reactions has taken place, the desired compounds are isolated from the reaction medium by extraction and separated by column chromatography or preparative layer chromatorgraphy, preferably on silica gel.

The process according to the invention gives, for example, the following compounds, which are red, amorphous substances, readily soluble in methanol, ethyl acetate, chloroform and toluene but insoluble in water and hexane, and which can be detected by thin layer chromatography on silica gel 60 $F_{254}$ (Merck), preferably with the mobile phase system chloroform/methanol=8/2.

CYTORHODIN SE

Rf value in the system mentioned: 0.69.
UV maxima: 234, 252 (Sch), 296 and 496 nm in methanol/10% 1N HCl.
NMR spectrum: FIG. 1.
$C_{48}H_{64}N_2O_{16}$ M calculated 924 (confirmed by FAB-MS).
cytorhodin SE has the formula I, in which $R_1$ denotes Roa and $R_2$ denotes Roa—Rod—Acu.

CYTORHODIN TF

Figure 2:
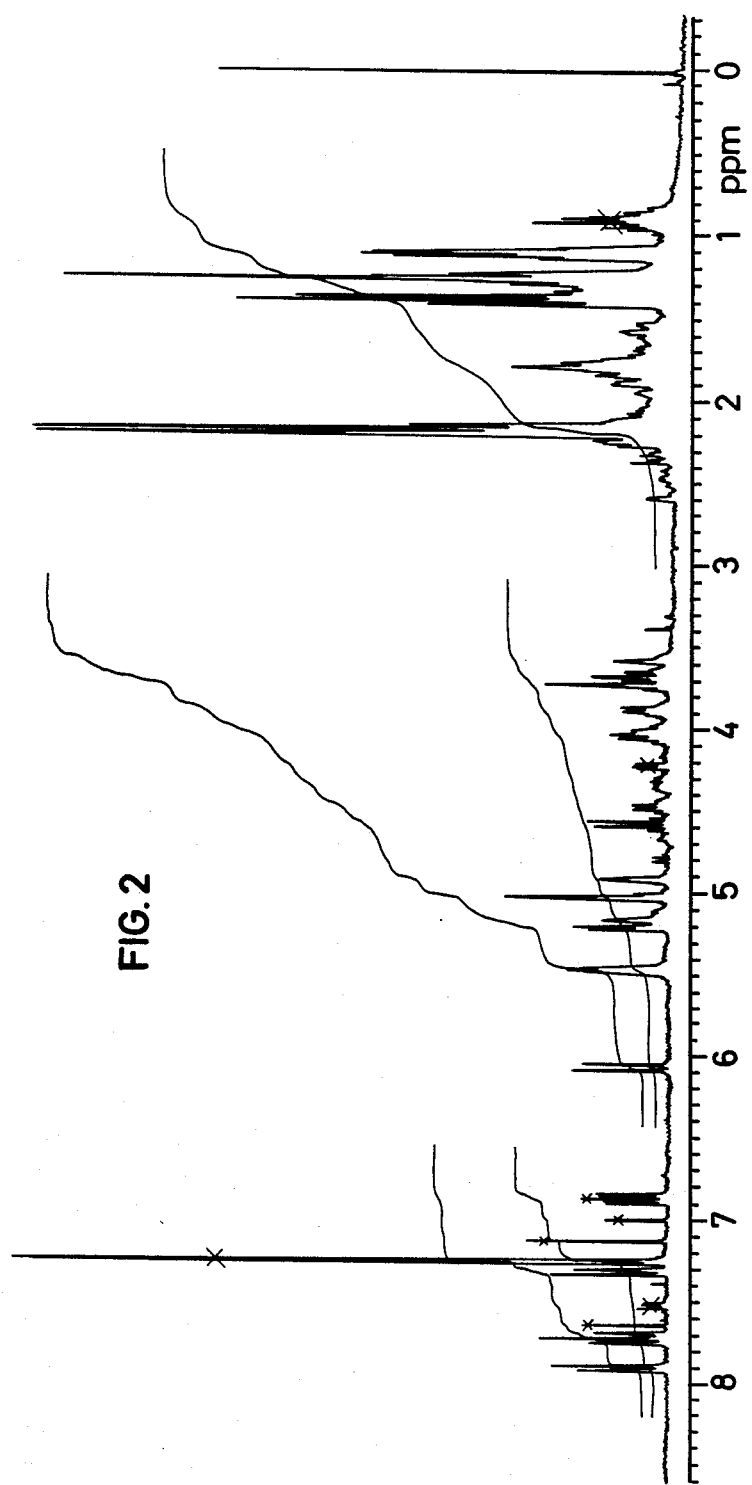

Rf value in the system mentioned: 0.49.
UV maxima: 235, 252 (Sch), 296 and 496 nm in methanol/10% 1N HCl.
NMR spectrum: FIG. 2.
$C_{48}H_{64}N_2O_6$ M calculated 924 (confirmed by FAB-MS).
cytorhodin TF has the formula I, in which $R_1$ denotes Roa—Rod—Acu and $R_2$ denotes Roa.

CYTORHODIN SD

Figure 3:
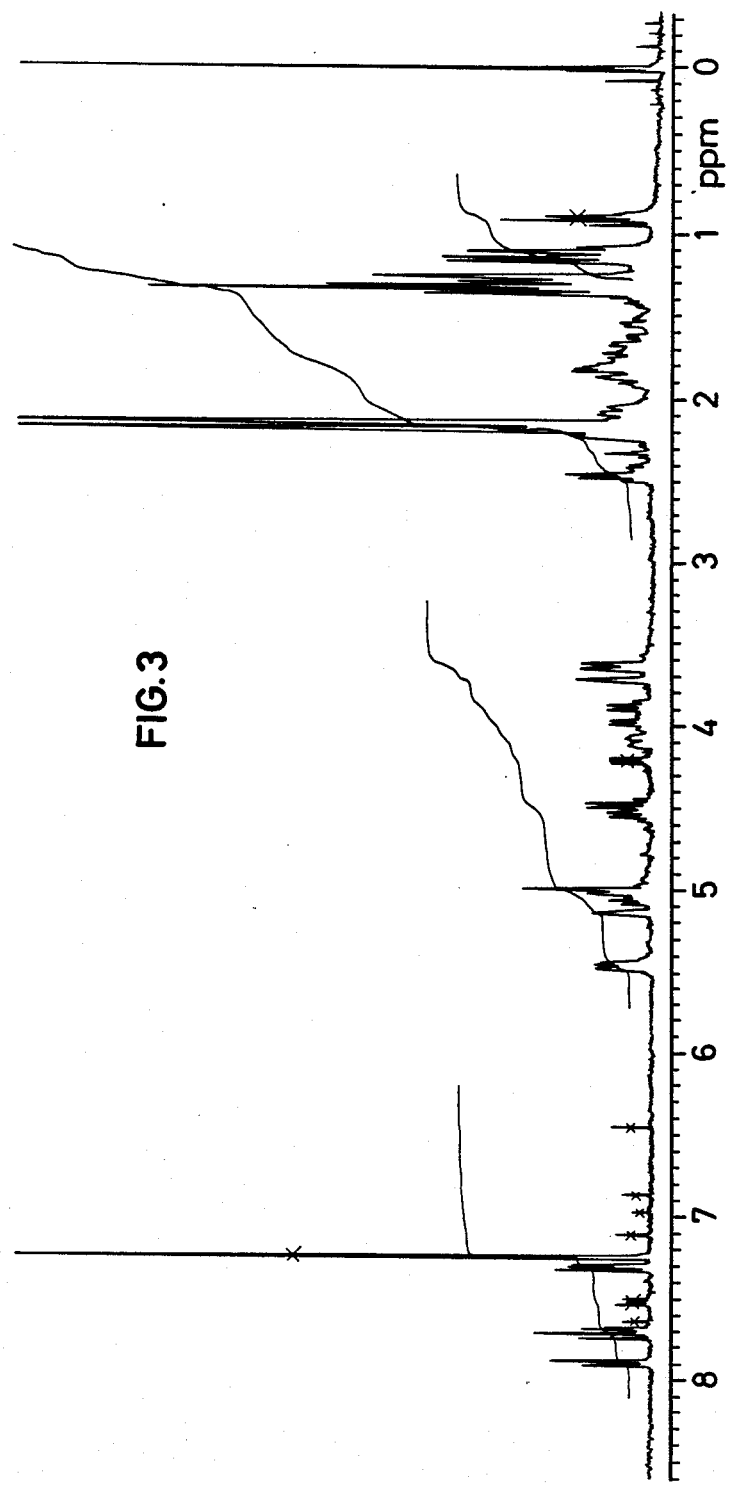

Rf value in the system mentioned: 0.61.
UV maxima: 234, 253 (Sch), 292 and 495 nm in methanol/10% 1N HCl.
NMR spectrum: FIG. 3.
$C_{48}H_{64}N_2O_{17}$ M calculated 942 (confirmed by FAB-MS).
cytorhodin SD has the formula I, in which $R_1$ denotes Roa and $R_2$ denotes Roa—dF—CinA.

The cytorhodins according to the invention are distinguished by a high cytostatic activity and show the following action in the cell proliferation test on L1210 leukemia cells:

|  | $IC_{50}$ ($\mu$m/ml) |
| --- | --- |
| cytorhodin SE gluconate | $6 \times 10^{-3}$ |
| cytorhodin TF gluconate | $2 \times 10^{-2}$ |
| cytorhodin SD gluconate | $2 \times 10^{-1}$ |

The inhibiting action was determined (cell proliferation test) as described below:

LD1210 cells in the exponential growth phase ($5 \times 10^3$/ml in RPMI 1640) are incubated in a microtiter plate with different concentrations of the test substance for 72 hours (37° C., 5% of $CO_2$, 95% relative atmospheric humidity). Controls comprise cells incubated only with fresh medium. All the determinations are carried out as 4-fold determinations. After 65 hours, 50 $\mu$l of C14-thymidine (1.5 $\mu$C/ml) are added in order to radiolabel the cell DNA. After incubation for 7 hours, the cells are filtered off with suction and the DNA is precipitated with 5% strength trichloroacetic acid and washed with water and methanol in succession. After drying at 50° C., the radioactivity incorporated into the DNA is determined after addition of 5 ml of scintillation liquid. The results are stated as ratios of the scintillation index after incubation with the test substance in percent of the untreated control. From the measurement values thus obtained, the dose/effect curve is determined, and the $IC_{50}$, that is to say the concentration which reduces the incorporation of radioactive thymidine by 50% under test conditions in comparison with the control, is determined graphically.

As stated above, the compound according to the invention have a cytostatic activity, that is to say a therapeutic action against tumors, in particular malignant tumors, in humans and animals.

The compounds and the acid addition salts can therefore be used as medicaments for the treatment of tumors. The compounds can be administered in various ways, depending on the dosage form. The compounds are usually administered as a mixture with pharmaceutically customary excipients or diluents. Thus, for example, they can be administered individually or as a mixture together with excipients such as maltose or lactose, or as non-toxic complexes, for example as a deoxyribonucleic acid complex.

A typical mode of administration is injection of a solution of the compound according to the invention is distilled water or physiological saline solution. The solutions can be injected intraperitoneally, intravenously or intraarterially.

The daily dose and unit dose can be determined from animal experiments and also from in vitro tests so that the total dose which is administered continuously or at intervals does not exceed a previously specified range. Thus, the total dose for one treatment cycle is about 0.5–5 mg/kg of body weight. This dose can be administered in appropriate fractions over a period of 7 days. It is clear, however, that the particular doses which can be individually specified for the treatment of humans or animals depend on the particular situation, for example the age, body weight, sex, sensitivity, diet, time of administration, other medicaments administered, physical condition of the patient and severity of the illness.

The preparation of the compounds according to the invention is described in the following examples.

EXAMPLE 1

1.1 g of cytorhodin F were dissolved in 250 ml of 0.1N hydrochloric acid and the solution was stirred at room temperature for 115 minutes. The pH was brought to 3 with 1N sodium hydroxide solution and the mixture was extracted three times with 250 ml of chloroform each time. Extraction three times with 250 ml of chloroform each time was carried out analogously at pH 5.5 and pH 7, which were likewise established by addition of 1N sodium hydroxide solution. The extracts at pH 3 and pH 7 contained unreacted educt and $\beta$-rhodomycin II, which is formed as a secondary product of hydrolysis and has already been described by Brockmann et al. (Naturwissenschaften 42, 492 (1950); and Chem. Ber. 86, 261, (1953)). The solution extracted at pH 5.5 was dried over sodium sulfate and concentrated to a residue of 380 mg.

The residue was chromatographed on 70 g of silica gel (60, 15–40 μm, Merck) over a medium pressure column of 120 ml (Labomatic). The solvent mixture chloroform/methanol/glacial acetatic acid/water=70/20/10/2 was used for this 190 fractions of 5 ml were selected at a flow rate of 2 ml/minute, and, after testing by analytical HPLC (Li-Chrosorb Si60, 5 μm, Merck, using the system chloroform/methanol/glacial acetic acid/water/triethylamine=750/100/100/20/0.5), were combined as follows:

| fractions | 58–88 | 45 mg | cytorhodin SE |
| fractions | 89–119 | 40 mg | cytorhodins SE and TF |
| fractions | 120–190 | 81 mg | cytorhodin TF |

A 5% strength aqueous solution of $Na_2HPO_4$ was added to the combined fractions, until the chloroform phase separated out, in order to obtain the dry substances, the chloroform phase was washed with one volume of $Na_2HPO_4$ solution and with water, dried over sodium sulfate and concentrated in vacum and the residue was precipitated with hexane.

To test for cytostatic activity, the pure substances were converted into the corresponding readily water-soluble D-gluconates with gluconic acid lactone.

EXAMPLE 2

100 mg of cytorhodin P were dissolved in 10 ml of 0.1N HCl, the reaction solution was stirred at room temperature for 3.5 hours, the pH was then brought to 7.5 with 0.1N NaOH and the solution was shaken three times with 10 ml of $CHCl_3$ each time. The combined organic phase were washed neutral with a little water, dried over sodium sulfate and evaporated in vacuo.

According to thin layer chromatography, the dry residue (68 mg) contained, in addition to polar β-rhodomycin II, two less polar main products, and the mixture was separated by preparative layer chromatography. For this, 10 mg portions of the residue, dissolved in $CHCl_3$, were applied to a silica gel 60 thin layer chromatography aluminum foil, 0.2 mm, 20 cm×20 cm, Merck, and chromatographed with the lower phase of the solvent mixture $CHCl_3$/methanol/water 130/40/70.

The bands scraped off were eluted with $CHCl_3$/methanol 1:1 and the eluate was evaporated in vacuo. After the residue had been taken up in a little $CHCl_3$, it was filtered over a glass frit and the filtrate was evaporated to dryness in vacuo. 5 mg of cytorhodin SD and 2.5 mg of cytorhodin TF were obtained.

Cytorhodin SD gave the readily water-soluble D-gluconate with D-gluconic acid lactone.

We claim:

1. A compound of the formula I

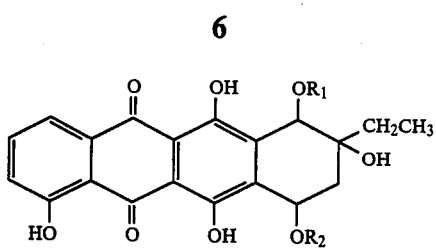

in which $R_1$ and $R_2$ are different and one of the radicals represents the sugar residue Roa of the formula

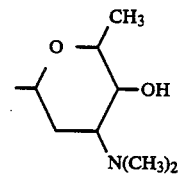

while the other radical represents the sugar combination —Roa—Rod—Rod of the formula

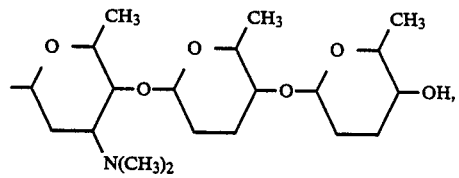

—Roa—Rod—Acu of the formula

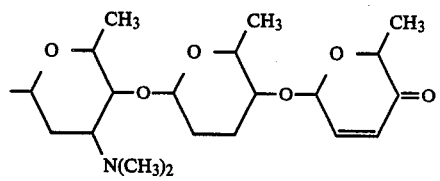

—Rod—dF—CinA of the formula

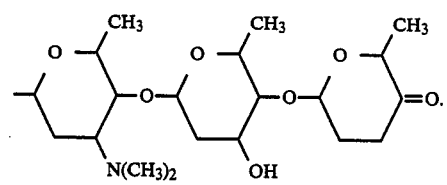

2. The compound of the formula I as claimed in claim 1, in which $R_1$ denotes Roa and $R_2$ denotes Roa—Rod—Rod.

3. The compound of the formula I as claimed in claim 1, in which $R_1$ denotes Roa—Rod—Rod and $R_2$ denotes Roa.

4. The compound of the formula I as claimed in claim 1, in which $R_1$ denotes Roa and $R_2$ denotes Roa—Rod—Acu.

5. The compound of the formula I as claimed in claim 1, in which $R_1$ denotes Roa—Rod—Acu and $R_2$ denotes Roa.

6. The compound of the formula I as claimed in claim 1, in which $R_1$ denotes Roa and $R_2$ denotes Roa—dF—CinA.

7. The compound of the formula I as claimed in claim 1, in which $R_1$ denotes Roa—dF—CinA and $R_2$ denotes Roa.